(12) United States Patent
Bader et al.

(10) Patent No.: US 10,377,681 B2
(45) Date of Patent: Aug. 13, 2019

(54) USE OF AN ADVANCED MULTIVARIABLE CONTROLLER TO CONTROL ALPHABUTOL UNITS

(71) Applicant: AXENS, Rueil Malmaison (FR)

(72) Inventors: Jean-Marc Bader, Taluyers (FR); Damien Maintenant, Bouafle (FR)

(73) Assignee: AXENS, Rueil Malmaison (FR)

( * ) Notice: Subject to any disclaimer, the term of this patent is extended or adjusted under 35 U.S.C. 154(b) by 0 days.

(21) Appl. No.: 15/367,365

(22) Filed: Dec. 2, 2016

(65) Prior Publication Data
US 2017/0158581 A1    Jun. 8, 2017

(30) Foreign Application Priority Data

Dec. 3, 2015    (FR) ..................................... 15 61827

(51) Int. Cl.
| | | |
|---|---|---|
| C07C 2/26 | (2006.01) | |
| C07C 2/32 | (2006.01) | |
| G05D 7/06 | (2006.01) | |
| B01J 31/00 | (2006.01) | |
| C07C 11/08 | (2006.01) | |
| G05B 13/04 | (2006.01) | |
| G05D 16/20 | (2006.01) | |
| G05D 23/19 | (2006.01) | |

(52) U.S. Cl.
CPC .................. *C07C 2/26* (2013.01); *B01J 31/00* (2013.01); *C07C 2/32* (2013.01); *G05B 13/048* (2013.01); *G05D 7/0617* (2013.01); *G05D 16/20* (2013.01); *G05D 23/1917* (2013.01); *C07C 2531/14* (2013.01); *G05B 2219/32135* (2013.01); *Y02P 20/584* (2015.11)

(58) Field of Classification Search
None
See application file for complete search history.

(56) References Cited

U.S. PATENT DOCUMENTS

2016/0310936 A1 * 10/2016 Schmidt .................. C08F 10/08

FOREIGN PATENT DOCUMENTS

WO     WO 2013116922 A1 *  8/2013  ............... C07C 2/32

OTHER PUBLICATIONS

Choudhary et al., "Dynamic Simulation of Reactor to Produce 1-Butene by Dimerization of Ethylene", International Journal of Scientific & Engineering Research, vol. 3, Issue 6, p. 1-7, Jun. 2012.*

* cited by examiner

*Primary Examiner* — In Suk C Bullock
*Assistant Examiner* — Ali Z Fadhel
(74) *Attorney, Agent, or Firm* — Millen White Zelano and Branigan, PC; John Sopp

(57) ABSTRACT

The present invention describes a control system for units for the production of 1-butene by the oligomerization of ethylene in the presence of a homogeneous catalyst, in the liquid phase and at the bubble point, which uses a multivariable predictive controller and provides the units with better stability.

7 Claims, 5 Drawing Sheets

USE OF AN ADVANCED MULTIVARIABLE CONTROLLER TO CONTROL ALPHABUTOL UNITS

FIELD OF THE INVENTION

The present invention relates to the field of advanced process control, APC, and the regulation of industrial units. More particularly, it relates to oligomerization units operated in the presence of a homogeneous catalyst in the liquid phase and at the bubble point, the catalyst being soluble in the reaction phase. Preferably, the process in accordance with the invention is applicable to the oligomerization process for the production of 1-butene starting from ethylene.

EXAMINATION OF THE PRIOR ART

The patent EP 2 239 639 B1 describes a process for monitoring and regulating an industrial unit that employs a closed-loop identification phase for the operating parameters of the unit. That process is implemented by means of a multivariable controller.

In the present invention, the unit is modelled by a dynamic model in which the three target variables are the butene production rate, the temperature and the pressure of the reactor, and the four action variables are the flow rate of feed, the flow rate of cooling water which is supplied to the exchangers of the catalyst recycling loop or loops and the two flow rates for the two constituents of the catalyst or, amounting to the same thing, the flow rate of one of the constituents of the catalyst and the ratio between the flow rate of that constituent of the catalyst and that of the other constituent.

Without APC, i.e. in accordance with the prior art, the usual mode for regulating the units for the production of 1-butene by the oligomerization of ethylene may vary as a function of the units:

In a first regulation mode, the ratio of the flow rates of catalyst, T2/LC, is kept fixed, and the flow rate of the constituents T2 or LC of the catalyst is variable. Usually, the flow rate of the constituent T2 is adjusted in order to control the productivity of the unit. In that regulation mode, the flow rate of ethylene is not manually modified as it is cascaded with the reactor pressure control. The term "cascaded" means the fact that, in contrast to a simple PID regulation in which an action variable (Vact) acts directly to maintain a target variable (Vtar), the target variable (Vtar) is kept constant via another target variable (Vtar2) which is itself under the control of another action variable (Vact2).

In a second regulation mode, the ratio of the floe rates of the catalyst, T2/LC, is modified in order to control the production of 1-butene. The ethylene flow rate is cascaded with the pressure control of the reactor.

The operator generally proceeds by varying the flow rate of each constituent of the catalyst in steps, each step corresponding to a percentage point, generally in the range 3% to 20%, more preferably in the range 5% to 12%, in order to limit the pressure fluctuations in the reactor.

A variation in the flow rate of the catalyst causes relatively rapid effects in the reactor of the unit, but because the overall dwell time in the unit is more than a few hours, it is necessary to wait for a period of time in the range 3 hours to 10 hours, depending on the case, in order to discern the effects of these variations at the outlet from the unit. An advanced control system can be used to overcome this difficulty.

Depending on the units, there may be one to three catalyst recycle loops. In the two regulation modes described above, the temperature is kept constant by acting on the flow rate of cooling liquid which is supplied to the exchanger or exchangers of the catalyst recycle loop or loops. The majority of oligomerization reactions also result in the formation of polymers which are capable of becoming deposited in the cold sections, and in particular the exchangers, which brings about a variation in the exchange coefficient and a drop in efficiency.

The right hand graph is in accordance with the invention, i.e. with application of the APC, and the left hand graph is in accordance with the prior art. A remarkable stabilization of the two target variables: the reactor pressure and the 1-butene production—will be observed on the right hand graph.

Figure 5:
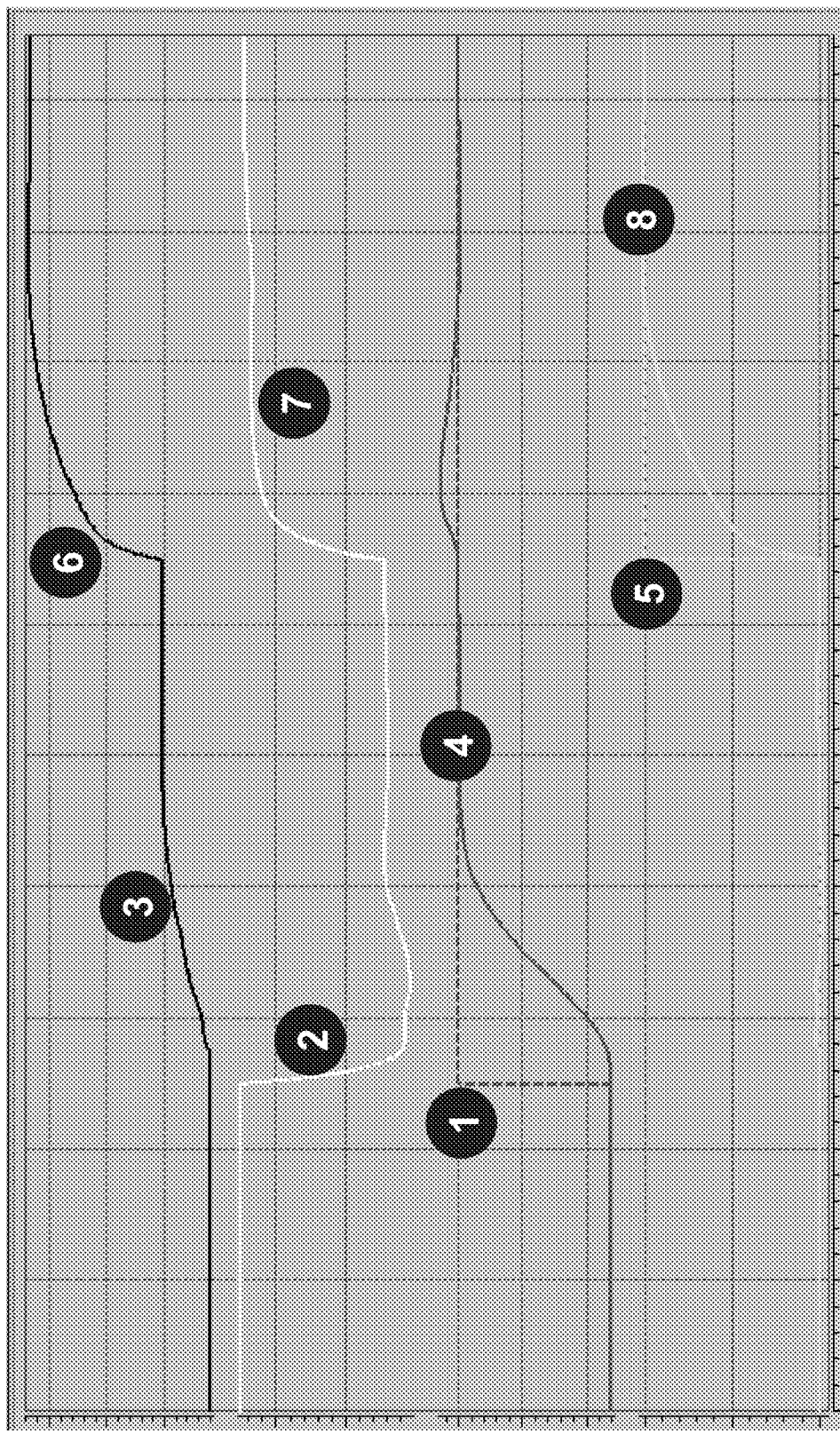

FIG. 5 shows how the two action variables, the feed flow rate (denoted 3 then 6) and the ratio between the two catalyst flow rates (denoted 2 then 7), act to carry out a change in the setpoint value of two of the target variables: butene production flow rate (denoted 5 then 8) and reactor pressure (denoted 1 then 4).

BRIEF DESCRIPTION OF THE INVENTION

Implementing an advanced process control in accordance with the invention, i.e. with APC, means that multivariable regulation can be carried out, by means of which the reactor temperature (Treac), the reactor pressure (Preac) and, as a consequence, the productivity of the unit (Dprod) are much more stable.

The process in accordance with the invention uses a multivariable controller. Dynamic modelling of the process for the production of 1-butene by the oligomerization of ethylene has meant that a novel advanced control strategy can be determined, which will hereinafter by termed the "advanced process control in accordance with the invention", which differs substantially from the strategies which are conventionally employed to operate this type of unit.

In accordance with the present invention, the 3 parameters which are intended to be kept constant, known as the target variable, are the reactor pressure (Preac), the reactor temperature (Treac) and the flow rate of the 1-butene produced (Dprod).

The 4 action variables which are acted upon with a view to keeping the target variables constant are: the ethylene flow rate (Dch), the flow rates of the two catalyst components (T2 and LC) and the flow rate of the cooling liquid which is supplied to the exchanger or exchangers of the catalyst recycle loops.

More precisely, the advanced process control (APC) in accordance with the invention uses a multivariable controller (termed the APC controller) which is based on 3 principles:

controlling the reactor pressure (Preac) by varying the quantity of catalysts injected (T2 or LC) by acting on the feed flow rate (Dch) in order to compensate for the effects of pressure on the conversion which affects the production flow rate (Dprod), controlling the production flow rate (Dprod) by the feed flow rate, by acting on the catalyst flow rate (LC or T2) in order to compensate for the effects on the pressure, controlling the reactor temperature (Treac) by acting on the flow rate of the cooling liquid which is supplied to the exchanger or exchangers of the catalyst recycling loop or loops.

The APC controller is installed in a computer which is connected to the system controlling the process in the industrial unit, said computer carrying out the following operations:

recovering signals for the action variables and the target variables, generating new setpoints for the action variables, and sending the new setpoints to the process control system.

In accordance with a first variation of the advanced process control in accordance with the invention, the ratio of the two components of the catalyst, T2/LC, is fixed and only the flow rate of the component T2 is acted upon. In this case, the ratio (LC/T2) is kept between 1.5 and 3 moles/moles, more particularly between 1.9 and 2.5 moles/moles, and highly preferably between 2 and 2.2 moles/moles in order to limit the formation of polymers.

In accordance with a variation of the advanced process control in accordance with the invention, the flow rates of the catalysts, T2 and LC, vary freely within a range such that the ratio (T2/LC) is kept between 1.5 and 3 moles/moles, more particularly between 1.9 and 2.5 moles/moles, and highly preferably between 2 and 2.2 moles/moles in order to limit the formation of polymers.

In a routine functional mode of the advanced process control in accordance with the invention:

upon a change in the pressure setpoint, at constant production, the flow rate of the constituents of the catalyst is modified in order to control variations in the pressure and the modification of the feed flow rate compensates for the change in conversion (and thus in production) generated by the new pressure setpoint, upon a change in the production setpoint, at constant pressure, the feed flow rate is modified in order to control the variation in production, and the modification of the flow rate of the two components of the catalyst compensates for the effects of the change of pressure generated by the new production setpoint.

In order to obtain the advanced process control in accordance with the present invention, parameterization of said advanced process control is carried out in advance by obtaining experimental data, said experimental data deriving from a campaign of tests consisting of generating variations in the action variables and following the responses of the unit on the target variables, variations in the action variables and responses of the target variables being treated in multivariable identification software.

The present invention also concerns the application of the advanced process control to a process for the oligomerization of ethylene in order to produce 1-butene, preferably operated under the following conditions:

pressure in the range 0.5 to 8 MPa, preferably in the range 1 to 4 MPa, temperature in the range 20° C. to 150° C., preferably in the range 30° C. to 100° C.

Catalysts which may be used in the process in accordance with the invention have, for example, been described in patent documents EP-A-2 388 069 and EP-B-0 885 656; their descriptions are hereby incorporated by reference.

Preferably, the catalyst comprises a first constituent based on titanium or chromium, more preferably based on titanium, and a second constituent based on aluminium.

DETAILED DESCRIPTION OF THE INVENTION

For good comprehension of the invention, the function of the process for the oligomerization of ethylene into 1-butene in a reactor operated in the liquid phase at the bubble point in the presence of a homogeneous catalyst should be recalled.

In an industrial unit, once the temperature and the level of the liquid phase in the reactor have been adjusted correctly, it is important to control two other parameters:

the reactor pressure, which must remain within design specifications or suffer a major loss of selectivity, the 1-butene production, which must be adapted to the requirements of the downstream fabrication units.

In the advanced process control in accordance with the invention (with APC), the use of a dynamic model in a multivariable predictive controller means that the following strategy can be employed, illustrated by the closed loop dynamic simulation below:

Controlling the reactor pressure by varying the quantity of catalysts injected by acting on the feed flow rate in order to compensate for the effects of pressure on the conversion which affects the production.

Controlling the production by the feed flow rate, by acting on the quantity of catalyst in order to compensate for the effects on the pressure.

Controlling the temperature by acting on the flow rate of the cooling liquid which is supplied to the exchanger or exchangers of the catalyst recycling loop or loops.

In the case of deposition of polymer in the loop exchanger or exchangers, the multivariable controller of the advanced process control can also, be used to anticipate a reduction in the efficiency of those exchangers.

One example of a simulation in accordance with the APC process of the invention, given here by way of illustration, can be summarized by the following points (the numerals which appear in the description below are given with reference to FIG. 5):

upon a change in the pressure setpoint (1), at constant production, the flow rate of the constituents of the catalyst is modified (2) in order to control variations in the pressure. Furthermore, modification of the feed flow rate (3) compensates for the change in conversion (and thus in production) generated by the new pressure setpoint (4), upon a change in the production setpoint (5), at constant pressure, the feed flow rate is modified (6) in order to control the variation in production, and the modification of the flow rate of the catalyst (7) compensates for the effects of the change of pressure generated by the new production setpoint (8).

In this example, temperature control is not represented. Any variation in conversion affecting the exothermicity, and thus the temperature of the reactor, and the flow rate of cooling water will be adjusted as a consequence.

By using APC:

Regulating the catalyst flow rate means that perturbations which affect the pressure can be minimized. The pressure is stable.

The feed flow rate and the associated production are stable.

The temperature is more stable than with conventional regulation systems because the efficiency losses of the exchanger or exchangers has been anticipated.

In the regulation system in accordance with the invention, termed the APC system, the direct proportionality link which exists between the ethylene feed flow rate and the 1-butene product flow rate is exploited.

Description of the Process for the Production of 1-Butene

Figure 1:
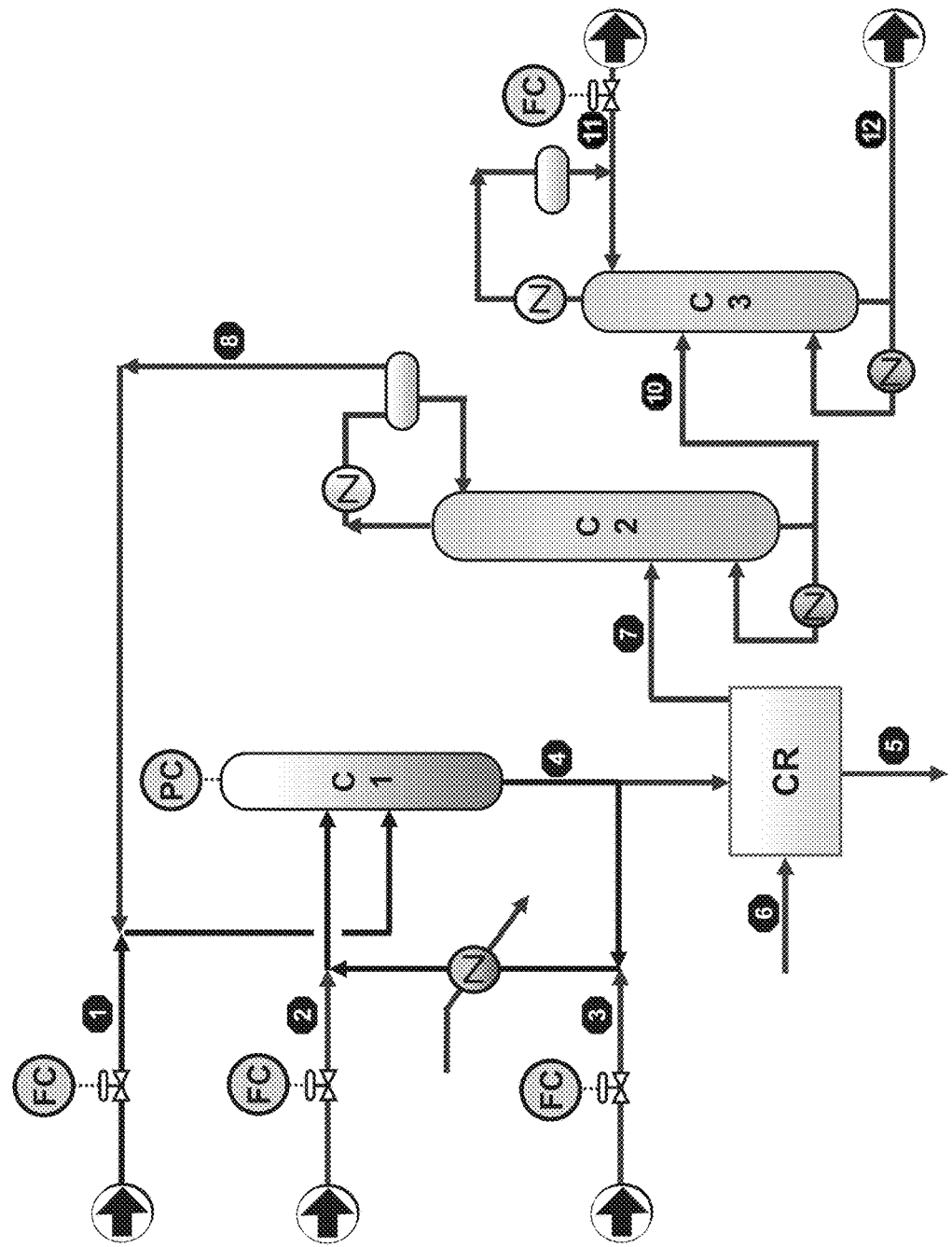
FIG. 1 represents the layout of a process for the oligomerization of ethylene into 1-butene, in which the principal streams, the reactor (C1) and the two distillation columns (C2 and C3) are highlighted. This layout also shows the principal elements of the control and regulation system in accordance with the invention, namely the systems for control or regulation of the action variables (flow rate of feed for the unit, flow rate of each catalyst, flow rate of cooling water) and the target variables (reactor pressure, flow rate of product, temperature of reactor).

FIG. 1 presents the principle of a typical layout of a process for the production of 1-butene starting from ethylene.

The process comprises a reactor (C1) supplied with a feed (1) essentially comprising ethylene. The reactor (C1) is also supplied with a homogeneous catalyst in suspension comprising two constituents (LC and T2) which are introduced separately into the reaction section via the respective streams 3 and 2.

Catalytic dimerization of the ethylene in the liquid phase is operated at a pressure in the range 0.5 to 8 MPa, preferably in the range 1 to 4 MPa, and at a temperature in the range 20° C. to 150° C., preferably in the range 30° C. to 100° C.

Since the reaction is exothermic, the temperature in the reactor is regulated by means of cooling a portion of the effluent in the loop comprising a water exchanger (E1) which has water as the cooling liquid.

The effluent from the reaction section (4) is then brought into contact with a catalyst inhibitor in a catalyst recovery zone (CR). Any catalyst inhibitor may be used in the process in accordance with the invention, in particular those described in the patent FR 2 733 497. A stream (4) of inhibitor is introduced into the catalyst recovery zone and a stream (5) of spent catalyst is recovered.

A concentrated catalytic solution is separated from the catalyst-free reaction effluent at (7) and said effluent (7) is sent to a fractionation section comprising a first column (C2) which can be used to separate unconverted ethylene (8) overhead, which is recycled to the reaction section, and the remainder of the effluent (10) from the bottom, which is supplied to the second separation column (C3).

The second fractionation column (C3) can be used to separate a cut comprising essentially 1-butene (11) which is the desired product, from the heavier oligomer, represented by the stream (12).

Description of the Advanced Process Control (APC)

The advanced process control in accordance with the invention, hereinafter termed APC, can in general be carried out in any unit operating in the liquid phase and at the bubble point starting from a gaseous feed, with a catalyst which is soluble in the liquid phase (homogeneous catalyst).

In the advanced process control in accordance with the invention, the operator defines the values for the target variables, and the APC takes all of the action variables into account; the operator no longer needs to be concerned about them. This strategy can be applied in order to obtain better stability for the unit during operation.

The parameterization of the advanced process control is carried out in advance by obtaining experimental data. These experimental data derive from a campaign of tests consisting of generating variations in the action variables. The responses of the unit to the target variables are then processed in multivariable identification software. Thus, for example, the time delay is obtained which corresponds to the time passed between the moment at which the action variable is manipulated and the onset of the response to the target variable; a time constant and a gain can be obtained which together define the dynamics of the change in the target variable taking into account the change in the setpoint of the action variable.

The reactor temperature ($T_{reac}$) is controlled by manipulating the flow rate controllers. Measuring it verifies that the temperature at the reactor bottom is at target (or at the setpoint value).

The inlet temperatures for the exchangers (E1) in the liquid recycle loop comprising the catalyst (known as pump-around in the art) in reactor (C1) are also controlled.

Analysis of the gaseous phase recycle can be used to determine the quantities of ethylene and 1-butene present.

The reactor pressure ($P_{reac}$) is controlled by acting on the flow rate of the components LC and T2 of the catalyst or by regulating both the flow rate of LC and the ratio T2/LC.

The conversion per pass is generally kept below 90%, preferably below 87%, in order to limit the risk of polymer formation.

The production is controlled by acting on the conversion per pass and the ethylene inlet flow rate.

The action variables can be used to simultaneously and continuously control the target variables, which is not possible without using an APC, because simple PID control does not function correctly to stabilize a target variable which depends on multiple parameters.

In addition, the flow rate of 1-butene produced ($D_{prod}$) is proportional to the entering ethylene feed flow rate, and manipulation thereof to control the reactor pressure ($P_{reac}$) is thus opposed to the control of the product flow rate ($D_{prod}$). Only by using multivariable APC can simultaneous and continuous control of all of the target variables be obtained.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 15/61.827, filed Dec. 3, 2015 are incorporated by reference herein.

Examples in Accordance with the Invention

An industrial unit for the production of 1-butene by the oligomerization of ethylene in accordance with the layout of FIG. 1 was equipped with an advanced process control system in accordance with the invention with the controllers mentioned in the description and shown in FIG. 1.

By operating the reactor at 2.1 MPa and at 52° C., with the first constituent of the catalyst being LC2253 sold by AXENS and the second constituent of the catalyst being TEA (TriEthylAluminium $(C_2H_5)_3Al$, diluted in n-hexane), the unit produced 3.0 t/h of 1-butene. This ratio was preferably kept to between 1.5 and 3 moles/moles, more preferably between 1.9 and 2.5 moles/moles and highly preferably between 2 and 2.2 moles/moles in order to limit polymer formation.

The APC controller was installed on a computer connected to the industrial unit process control system. The computer recovered signals for the action variables and the target variables, generated the new action variable setpoints and sent them to the process control system.

Figure 2A:
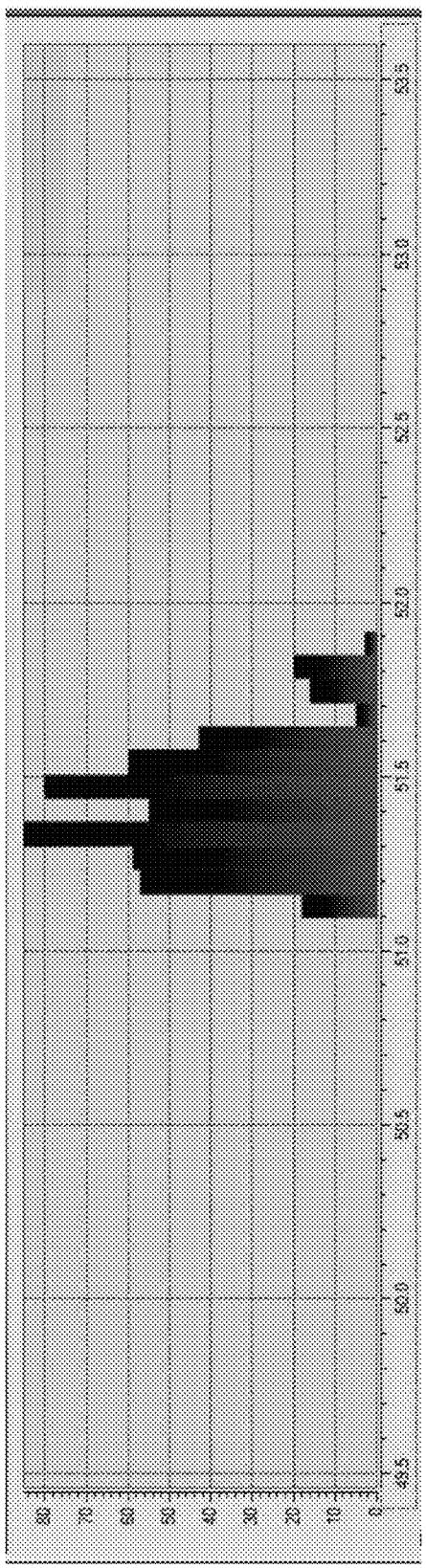
FIGS. 2a and 2b represent two histograms of the variation of the reactor temperature of the unit as a function of time. The graph of FIG. 2a is in accordance with the invention, i.e. with the application of APC, and the graph of FIG. 2b is in accordance with the prior art. The very substantial reduction in the dispersion of the values with the APC regulation system can be observed.
Figure 2B:
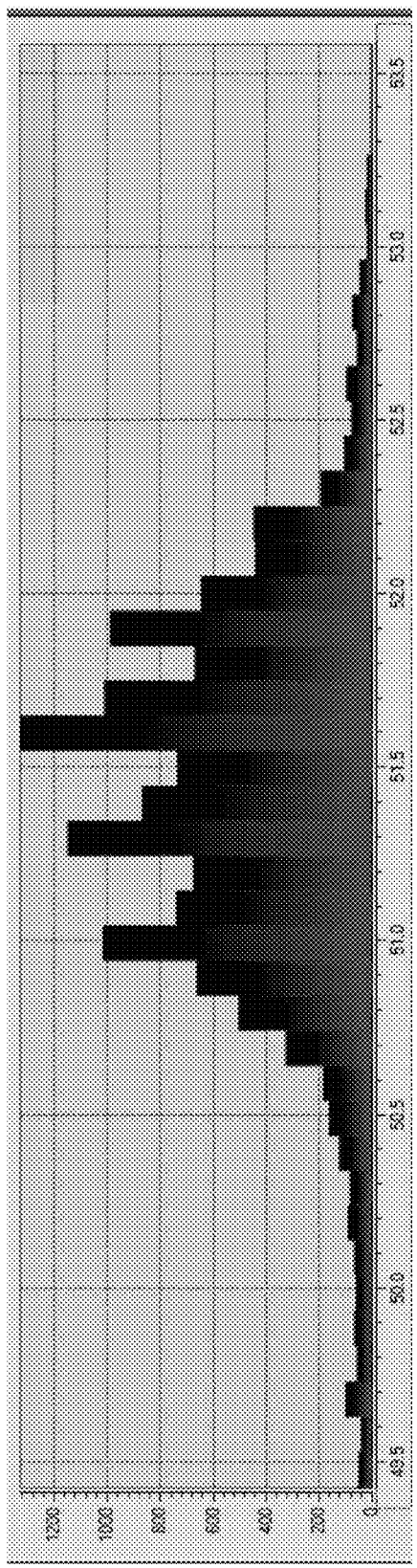

FIGS. 2a and 2b show that the advanced control system could be used to very efficiently regulate the reactor bottom temperature with variations in this bottom temperature which were 4 times smaller in the presence of advanced control compared with a unit which did not have advanced control.

Figure 3A:
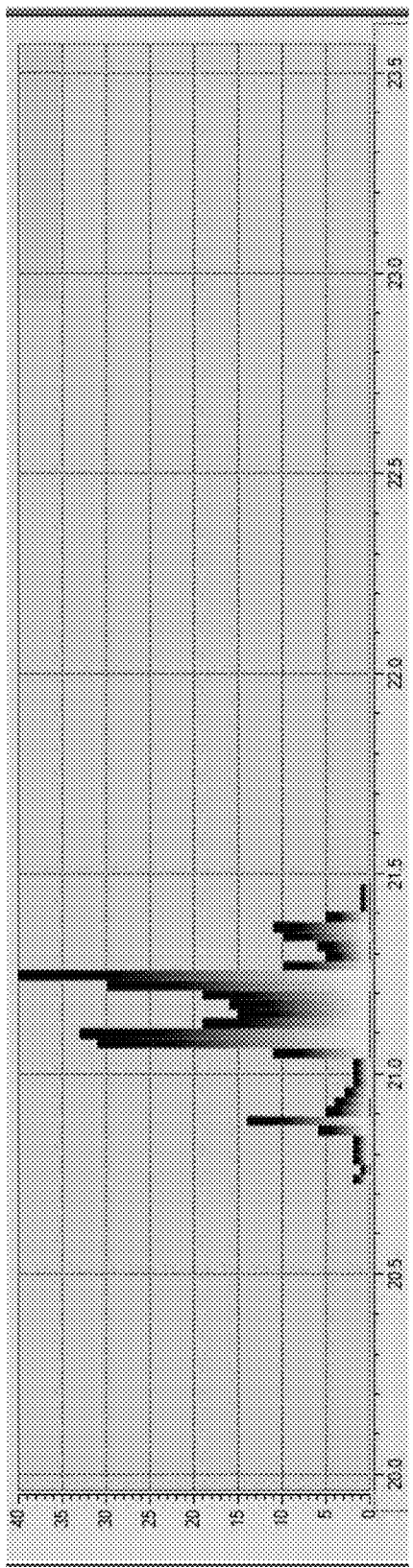
FIGS. 3a and 3b represent two histograms for the variation of reactor pressure over time. The graph of FIG. 3a is in accordance with the invention, i.e. with the application of APC, and the graph of FIG. 3b is in accordance with the prior art. The very substantial reduction in the dispersion of the values with the APC regulation system can be observed.
Figure 3B:
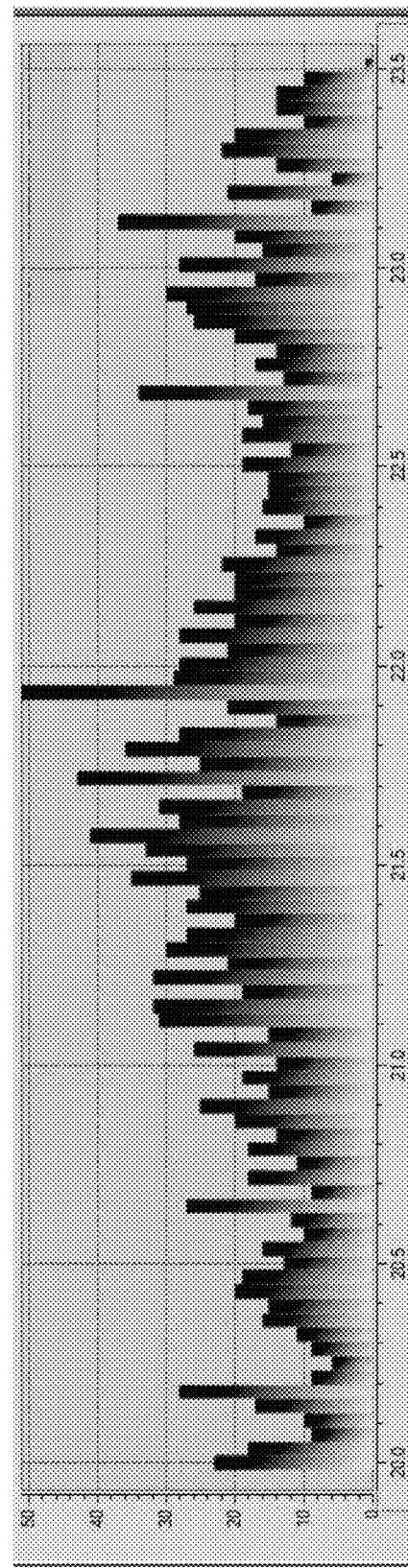

FIGS. 3a and 3b show a very good regulation of the reactor pressure, with a remarkable reduction in the range of variation of the value for this pressure over time, since the variation about the target value was reduced by a factor of 6 compared with that obtained with the prior art regulation system.

Figure 4:
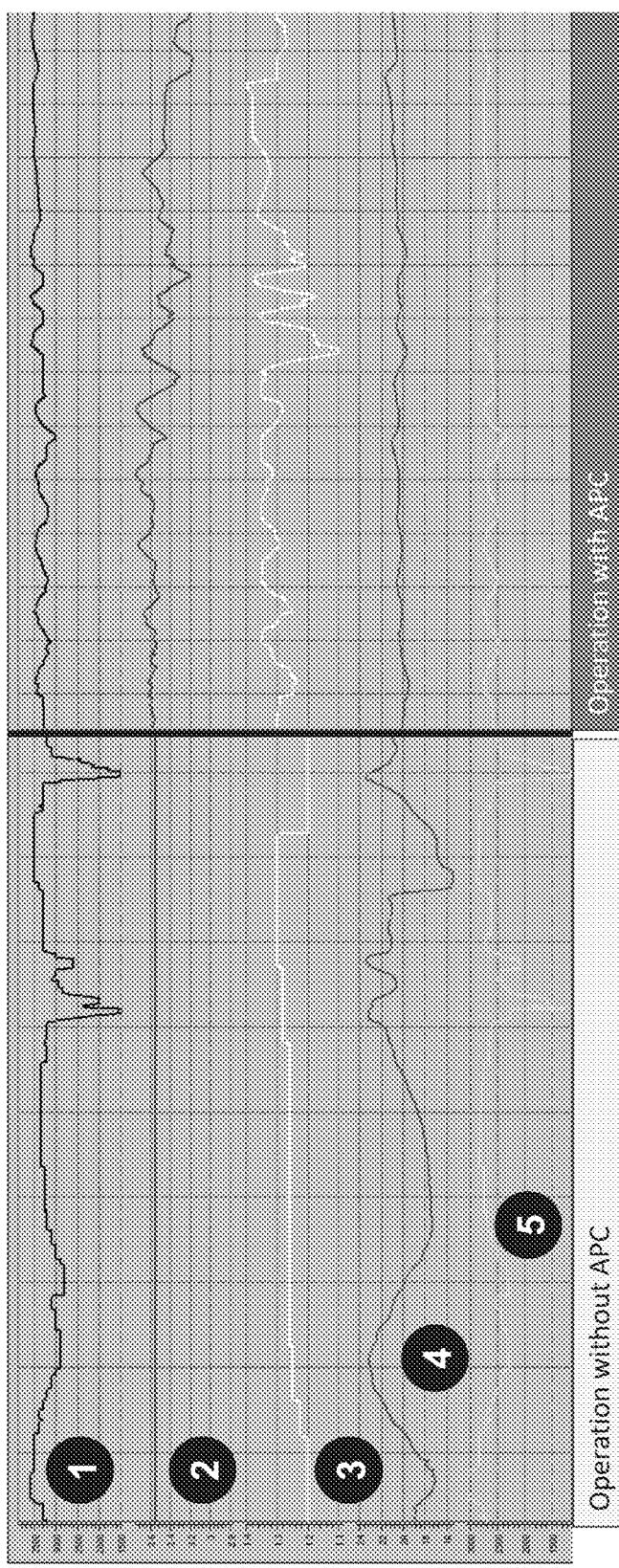
FIG. 4 represents the variation with time of the reactor pressure (denoted 4) and the flow rate of 1-butene production (denoted 5), as a function of the feed flow rate and the flow rate of the two constituents of the catalyst (respectively denoted 2 for T2 and 3 for LC).

FIG. 4 represents the variation with time of the pressure of the reactor and the 1-butene production flow rate as a function of the feed flow rate and the flow rate of the two catalysts.

The right hand graph is in accordance with the invention, i.e. with the application of APC, and the left hand graph is in accordance with the prior art.

With the system without APC regulation, it can be seen that the operator only manipulates the feed flow rate, and the catalyst flow rates only to a small extent. The flow rate of catalyst 1 remains almost constant. He has to make a compromise between controlling the production flow rate and that of the reactor pressure.

With the APC regulation system, it can be seen that the feed flow rates and the two catalysts are manipulated simultaneously and continuously in order to control the production flow rate and the reactor pressure. It can also be seen, and this is the major advantage of the system of the invention, that the production flow rate and the reactor pressure are effectively much better controlled, i.e. each is maintained to very close to the setpoint value.

FIG. 5 shows the action of two of the action variables: the feed flow rate (denoted 3 then 6) and the ratio between the two catalyst flow rates (denoted 2 then 7), in order to operate a change in the setpoint value on two of the target variables: production flow rate for butene (denoted 5 then 8) and reactor pressure (denoted 1 then 4).

The two changes on two of the target variables, namely the production of 1-butene and the reactor pressure, are taken charge of:
by the feed flow rate variable, initially by a very slow rise (denoted 3), then secondly by a more rapid rise (denoted 6),
by the variable which is the ratio of the catalysts, initially by a reduction in this value (denoted 2), then secondly by a rise in the value to substantially the same level as the starting value (denoted 7).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for advanced process control (APC) of an ethylene oligomerization unit having a reactor, a catalyst recycling loop or loops and a heat exchanger or exchangers for the catalyst recycling loop or loops, comprising:
oligomerizing an ethylene feed flow to 1-butene in the reactor operated in liquid phase and at bubble point and in the presence of a homogeneous catalyst having two components, while controlling oligomerizing target parameters simultaneously and continuously by adjusting action variables, wherein the two components of the catalyst comprise a first component (LC) comprising titanium or chromium and a second component (T2) comprising aluminum,
wherein the target parameters are production of 1-butene ($D_{prod}$), reactor pressure ($P_{reac}$) and reactor temperature ($T_{reac}$), and the action variables are ethylene feed flow rate ($D_{Ch}$), flow rate of each of the components of the catalyst (T2 and LC) and flow rate of cooling liquid supplied to the exchanger or exchangers of the catalyst recycling loop or loops; and
wherein a multivariable controller (termed the APC controller) carries out the method for advanced process control (APC) including performing the following three actions:
controlling the reactor pressure ($P_{reac}$) by varying the flow rate of each of the two catalyst components and varying the feed flow rate in order to compensate for the effects of reactor pressure on the conversion which affects the production,
controlling the production ($D_{prod}$) by varying the feed flow rate and the flow rate of each of the two catalyst components in order to compensate for the effects on the reactor pressure,
controlling the reactor temperature ($T_{reac}$) by acting on the flow rate of the cooling liquid which is supplied to the exchanger or exchangers of the catalyst recycling loop or loops,
wherein the flow rates of the components of the catalyst, T2 and LC, are varied within a range such that the ratio (T2/LC) is kept between 1.5 and 3 moles/moles;
the APC controller being installed in a computer which is connected to the system controlling the process in the oligomerization unit, said computer carrying out the following operations:
recovering signals for the action variables and the target variables,
generating new setpoints for the action variables, and sending the new setpoints to the APC controller.

2. The method according to claim 1, in which:
upon a change in the pressure setpoint, at constant production, the flow rate of the constituents of the catalyst is modified in order to control variations in the pressure and the modification of the feed flow rate compensates for the change in conversion, and thus in 1-butene production, generated by the new pressure setpoint, and upon a change in the production setpoint, at constant pressure, the feed flow rate is modified in order to control the variation in production flow rate of 1-butene, and the modification of the flow rate of the two components of the catalyst compensates for the effects of the change of pressure generated by the new production setpoint.

3. The method according to claim 1, in which parameterization of the advanced process control is carried out in advance by obtaining experimental data, these experimental data deriving from tests consisting of generating variations in the action variables and the responses of the unit on the target variables being treated in multivariable identification software.

4. The method according to claim 1, wherein the oligomerization of ethylene in order to produce 1-butene is operated under the following conditions:
pressure in the range 0.5 to 8 MPa,
temperature in the range 20° C. to 150° C.

5. The method according to claim 1, in which the flow rates of the components of the catalyst, $T_2$ and LC, are varied within a range such that the ratio ($T_2$/LC) is kept between 1.9 and 2.5 moles/moles in order to limit the formation of polymers.

6. The method according to claim 1, in which the flow rates of the components of the catalyst, $T_2$ and LC, are varied within a range such that the ratio ($T_2$/LC) is kept between 2 and 2.2 moles/moles in order to limit the formation of polymers.

7. The method according to claim 1, wherein the oligomerization of ethylene in order to produce 1-butene is operated under the following conditions:
pressure in the range 1 to 4 MPa,
temperature in the range 30° C. to 100° C.

* * * * *